US012745924B2

(12) United States Patent
Smith

(10) Patent No.: US 12,745,924 B2
(45) Date of Patent: Sep. 29, 2026

(54) PATIENT MONITORING SYSTEM

(71) Applicant: PurePrevent LLC, Colorado Springs, CO (US)

(72) Inventor: Samuel Smith, Colorado Springs, CO (US)

(73) Assignee: PurePrevent LLC, Colorado Springs, CO (US)

( * ) Notice: Subject to any disclaimer, the term of this patent is extended or adjusted under 35 U.S.C. 154(b) by 364 days.

(21) Appl. No.: 18/396,814

(22) Filed: Dec. 27, 2023

(65) Prior Publication Data

US 2024/0225481 A1 Jul. 11, 2024

Related U.S. Application Data

(60) Provisional application No. 63/437,559, filed on Jan. 6, 2023.

(51) Int. Cl.

*A61B 5/11* (2006.01)
*A61B 5/00* (2006.01)
*G16H 40/63* (2018.01)

(52) U.S. Cl.

CPC .......... *A61B 5/1113* (2013.01); *A61B 5/0002* (2013.01); *A61B 5/1118* (2013.01); *A61B 5/6892* (2013.01); *A61B 5/7264* (2013.01); *A61B 5/746* (2013.01); *G16H 40/63* (2018.01); *A61B 2562/0219* (2013.01); *A61B 2562/0247* (2013.01); *A61B 2562/046* (2013.01); *A61B 2562/06* (2013.01)

(58) Field of Classification Search

None

See application file for complete search history.

(56) References Cited

U.S. PATENT DOCUMENTS

2014/0039351 A1* 2/2014 Mix ....................... G16H 40/20 600/587
2016/0256080 A1* 9/2016 Shen .................... A61B 5/6891

(Continued)

OTHER PUBLICATIONS

Smith + Nephew Technical Overview of the Leaf Patient Monitoring System, (c) 2020, 4 pages.

(Continued)

*Primary Examiner* — David Earl Ogg

(74) *Attorney, Agent, or Firm* — BLANK ROME LLP

(57) ABSTRACT

A patient movement monitoring system for a bed mattress having a first side, a second side, a head end side and a foot end. The system includes a first sensing device coupled at the first side of the bed mattress, a second sensing device coupled at the second side of the bed mattress, and a third sensing device coupled at the head end side of the bed mattress. The sensing devices each include an accelerometer, gyroscope, and vibration sensor. The accelerometer detects an intensity of patient movement in the bed mattress. The gyroscope detects a change in the angle of the bed mattress. The vibration sensor detects vibration of the bed mattress. And a pressure sensing array is coupled at the underside of the bed mattress to detect changes in pressure of the bed mattress. A processing device is in electronic communication with the sensing devices and pressure sensing array and generates an alert if the sensors don't detect patient movement within a predetermined time period.

17 Claims, 10 Drawing Sheets

(56) References Cited

U.S. PATENT DOCUMENTS

| | | | | |
|---|---|---|---|---|
| 2020/0390403 | A1* | 12/2020 | Halperin | G08B 21/0461 |
| 2021/0161462 | A1* | 6/2021 | Lafleche | A61B 5/6891 |
| 2023/0011717 | A1* | 1/2023 | Larson | A61B 5/6823 |
| 2023/0137904 | A1* | 5/2023 | Najafi | A61B 5/1113<br>345/419 |

OTHER PUBLICATIONS

Tracey L. Yap et al., Pressure Injury Prevention: Outcomes and Challenges to Use of Resident Monitoring Technology in a Nursing Home, J. Wound Ostomy Continence Nurs. 2019; 46(3); pp. 207-213.

Walgreen Health Solutions, PressureAlert, Smart Pressure Injury Prevention & Treatment Technology, 4 pages, downloaded Jan. 4, 2023.

Vista Medical, Ltd, BodiTrak Patient Sensing System, 2016, 2 pages.

Cognito Health, Inc., Sensible(R)Care System, 2 pages, downloaded Jan. 4, 2023.

* cited by examiner

PATIENT MONITORING SYSTEM

RELATED APPLICATIONS

This application claims the benefit of priority of U.S. Provisional Application No. 63/437,559, filed on Jan. 6, 2023, the entire content of which is relied upon and incorporated herein by reference in its entirety.

BACKGROUND

Pressure injuries, commonly called bed sores, form when pressure is applied on the same area of skin for an extended period of time. Usually, this occurs when patients have limited mobility and therefore remain in the same position for hours without moving. Current protocols call for at-risk patients to be turned or rotated every 2 to 4 hours. These protocols involve moving patients from the prone position, onto their side, and then back. Though many medical facilities have these protocols in place, pressure ulcers are still common; partially as a result of failure to completely adhere to these protocols. In addition, patients' mobility status is often not correctly assessed or changes quickly. When this happens, at risk patients may not be identified and as a result are not adequately rotated. Another reason that pressure injuries continue to occur at higher than acceptable rates is that patients misreport their own movement. For example, a patient may tell nursing staff that they have been able to shift their weight in bed when they are actually unable to do so. Adequate movement involves a patient shifting their weight from one part of the body to another. Examples of movements that shift weight include rolling over from the prone position to their side, rolling from their side to the prone position, sitting up, and getting out of bed.

It is common practice in hospitals to calculate Braden scores to assess a patients risk for developing pressure injuries. This score includes 6 sub-scores: mobility, activity, sensory perception, nutrition, moisture, and friction/shear. The mobility and activity score range from 1 (worst) to 4 (best) and are determined subjectively by the staff caring for the patient. Studies have shown poor correlation between actual patient movement and subjective mobility and activity scores.

This problem is extremely costly. Approximately 3 million patients in the United States are treated for pressure injuries annually, with costs of up to $26.8 billion a year to the US healthcare system. Studies have shown that most pressure injuries develop outside of the hospital; many of which occur in nursing homes.

Pressure injuries are especially devastating to the elderly population in nursing homes. Elderly patients who develop a pressure injury have a death rate as high as 60% within 1 year of discharge. Pressure injuries can start patients on a downward spiral can be difficult to recover from. Pressure injuries are also costly for nursing homes. They spend $3.3 billion each year treating pressure injuries. The intensive treatment needed for pressure injuries acquired in nursing homes is often not reimbursed by Medicaid because they are categorized as preventable injuries or "never events" by the government. This has a major impact because estimates suggest that 66% of nursing home residents pay for their stay using Medicaid funding. Additionally, over 17,000 lawsuits are filed every year related to pressure injuries acquired in nursing homes, making it the second most common claim for medical malpractice suits.

Leaf Patient Monitoring System, by Smith+Nephew, is a motion sensor that is attached to the skin of a patient's chest. It alerts the nursing staff when patients have not moved their chest for an extended period so that the patient can be turned. However, it has shown limited success and did not show a statistically significant change in pressure injury occurrence. One major reason that the Leaf system did not affect these outcomes is that most patients (63%) refused to wear the sensor. Unsurprisingly, they cited the sensor mounted to the skin on their chest as irritating and uncomfortable.

PRESSUREALERT by Walgreen Health Solutions features motion sensors that attach to up to 11 different parts of the body to track patient movement. The sensors are outfitted in dressings that are directly attached to the body. The system alerts staff when the patient does not move the part of their body that the sensor is attached to for an extended period of time.

The BodiTrak is a mattress cover with imbedded pressure sensors that maps pressure on the hospital bed. The product uses data from pressure sensors to create and display a pressure map. It also alerts staff to immobility using an algorithm based on the Reswick-Rogers curve, which considers time and pressure. Cognito 2.5 is a Sensor pad that goes under patient bedding and communicates to a control box, which sends data to the cloud and then to nurse's mobile device and the desktop application. It uses proprietary sensors to detect patient motion. Both the BodiTrak and Cognito 2.5 are designed to prevent pressure injuries and falls.

None of the described technologies measure motion using sensors that attach to the side of the patient's bed. The sensors in these products either attach to the patient themselves (Leaf Patient Monitoring System, PRESSUREALERT) or to the underside of the mattress (BodiTrak, Cognito 2.5).

SUMMARY OF THE INVENTION

A patient movement monitoring system for a bed mattress having a first side, a second side, a head end side and a foot end. The system includes a first sensing device coupled at the first side of the bed mattress, a second sensing device coupled at the second side of the bed mattress, and a third sensing device coupled at the head end side of the bed mattress. The sensing devices each include an accelerometer, gyroscope, and vibration sensor. The accelerometer detects an intensity of patient movement in the bed mattress. The gyroscope detects a change in the angle of the bed mattress. The vibration sensor detects vibration of the bed mattress. And a pressure sensing array is coupled at the underside of the bed mattress to detect changes in pressure of the bed mattress. A processing device is in electronic communication with the sensing devices and pressure sensing array and generates an alert if the sensors don't detect patient movement within a predetermined time period. In addition, the device provides a quantitative measure of immobility that can be used by providers to predict risk of pressure injury development.

These and other objects of the invention, as well as many of the intended advantages thereof, will become more readily apparent when reference is made to the following description, taken in conjunction with the accompanying drawings.

DETAILED DESCRIPTION OF THE INVENTION

Figure 1:
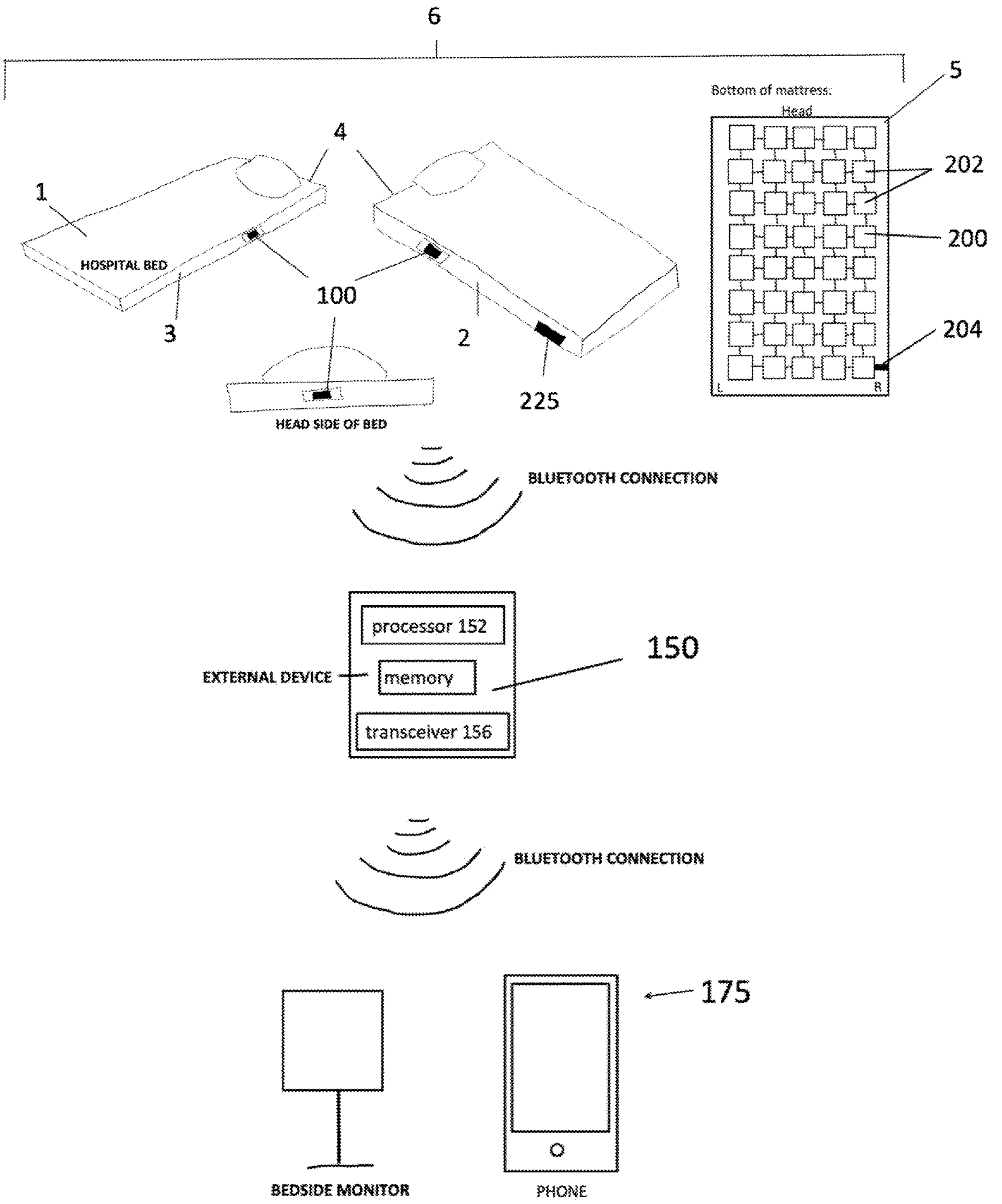
FIG. 1 is a block diagram of a pressure sensing system in accordance with the present disclosure.

In describing the illustrative, non-limiting embodiments illustrated in the drawings, specific terminology will be resorted to for the sake of clarity. However, the disclosure is not intended to be limited to the specific terms so selected, and it is to be understood that each specific term includes all technical equivalents that operate in similar manner to accomplish a similar purpose. Several embodiments are described for illustrative purposes, it being understood that the description and claims are not limited to the illustrated embodiments and other embodiments not specifically shown in the drawings may also be within the scope of this disclosure.

Turning to FIGS. 1-3, a patient monitoring system 6 is shown in accordance with one non-limiting illustrative example of the present disclosure. The system 6 includes one or more wireless sensing apparatus or devices 100 attached to a monitored device 1, pressure sensor grid 200, and a central processing unit 150 having a processor 152 in communication with the sensing devices 100 and 200. The system 6 is configured to detect patient immobility and alert nursing staff to the immobility.

Sensing Devices 100

The wireless sensing devices 100 are attached to the monitored device 1. The monitored device 1 can be, for example, a furniture item such as a bed or table, or an article of clothing, or any other suitable item such as a wheelchair or chair. In certain embodiments, the system 6 is especially useful to monitor a patient in a hospital bed. Accordingly, the monitored device 1 is a hospital bed mattress, which is part of a hospital bed having a bed frame. As shown in the example embodiment of FIG. 1, the bed mattress 1 includes a first side (i.e., right side) 2, a second side (i.e., left side) 3 opposite the first side 2, a head end side 4, and a foot end side. The mattress 1 also has a top surface and a bottom surface 5. The sides 2, 3, 4 are between the top surface and the bottom surface, and define a thickness of the mattress. Thus, the sides 2, 3, 4 extend substantially orthogonal to the top surface and the bottom surface 5. The mattress 1 also has a mattress (i.e., monitored device) head portion (e.g., the portion of the mattress 1 that aligns with the head of a patient in the mattress; for example, closest to the head end 4 of the mattress), a mattress torso portion (e.g., the portion of the mattress 1 that aligns with the torso of the patient in the mattress; for example, between the head portion and the midpoint of the mattress 1), and a mattress leg portion (e.g., the portion of the mattress 1 that aligns with the feet and/or legs of the patient in the mattress; for example between the torso portion and the foot end side).

A wireless sensing device 100 is attached to bed mattress 1 at the two sides (left side and right side) of the hospital bed mattress 1, and at the head end side 4 of the hospital bed mattress. One or more wireless sensing device(s) 100 are placed equidistant between the top surface and the bottom surface 5 of the hospital bed and lengthwise at the mattress head portion and/or at the mattress torso portion. The wireless sensing device 100 does not extend into the mattress. The wireless sensing device 100 can be affixed to any part of the bed in any suitable manner, such as by adhesive or fastener. Still further, the monitored device 1 can be a person, and the sensing device 100 can be affixed directly to the patient being monitored.

Figure 2A:
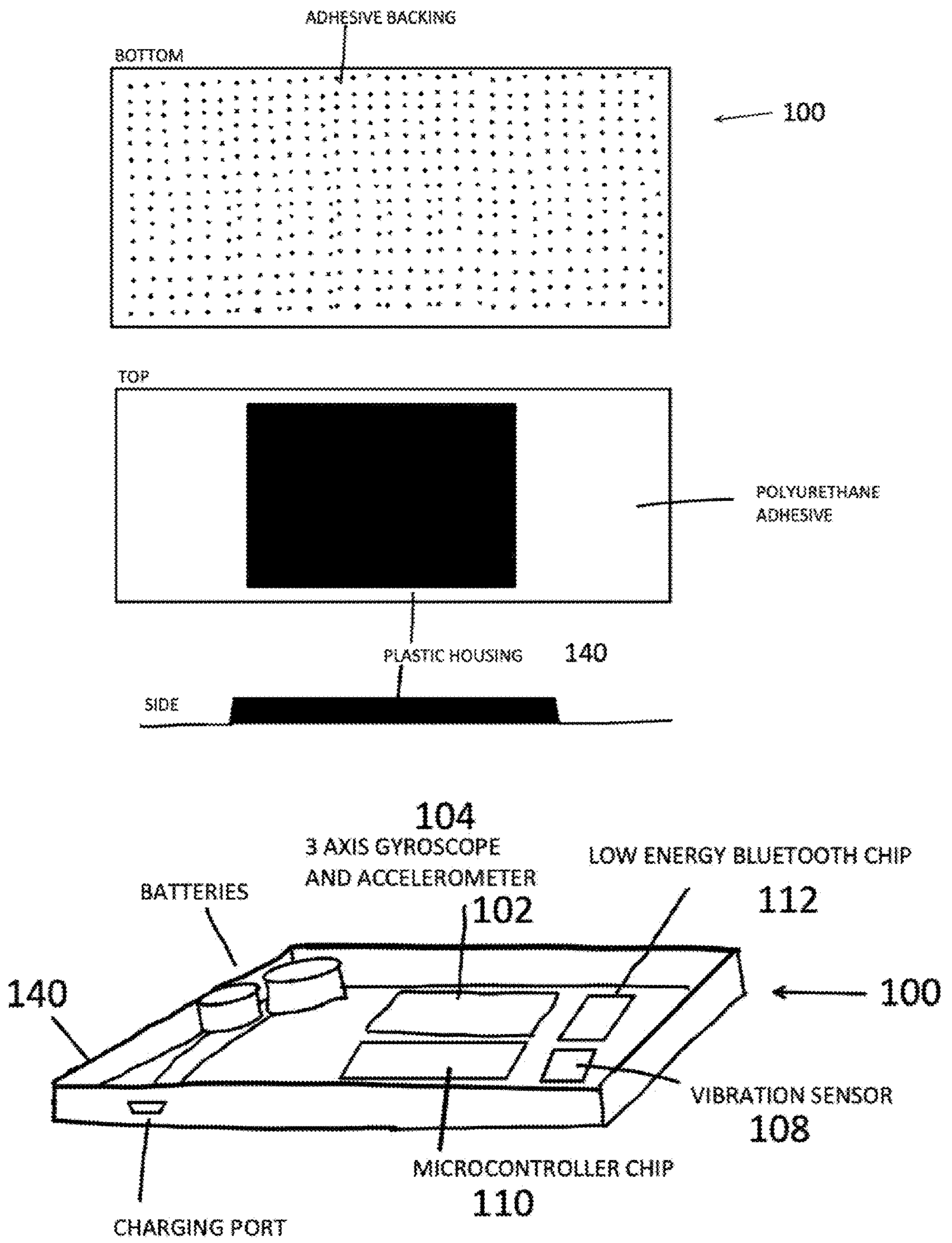
FIG. 2*a* is a block diagram of a wireless sensing apparatus having an accelerometer, gyroscope and vibration sensor.
Figure 3A:
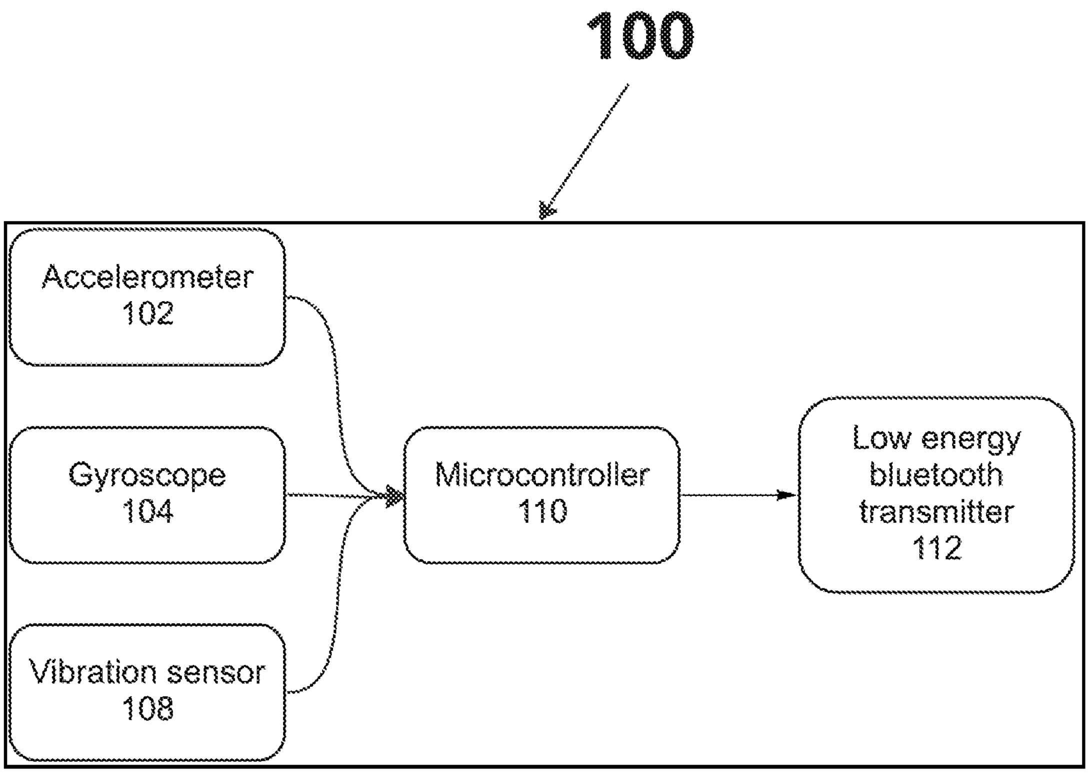
FIG. 3*a* is a block diagram of the wireless sensing apparatus of FIG. 2*a;*

As shown in FIGS. 2*a*, 3*a*, the wireless sensing device 100 includes one or more sensors, a microcontroller 110, and a wireless communication device 110. In certain embodiments, the sensors, controller 110 and communication device 110 are all contained within the same housing or enclosure; though in other embodiments each component can be positioned separately and in wired or wireless communication. The sensors include but are not limited to, an accelerometer 102, gyroscope 104, and vibration sensor 108 to measure deflections in the mattress caused by movement of the patient in the hospital bed 1. The sensor(s) 102, 104, 108 detect changes in the patient's position and different types of movement (e.g., rolling over, sitting up, getting out of bed). Each sensor(s) 102, 104, 108 detects the movement and provides (wired or wirelessly) a sensed output signal to the microcontroller 110. Sensors 102, 104, and 110 are all housed within the same apparatus 100. In certain embodiments, the individual sensing devices (e.g., the gyroscope and the accelerometer) are separate devices, but located within the same housing.

Figure 8:
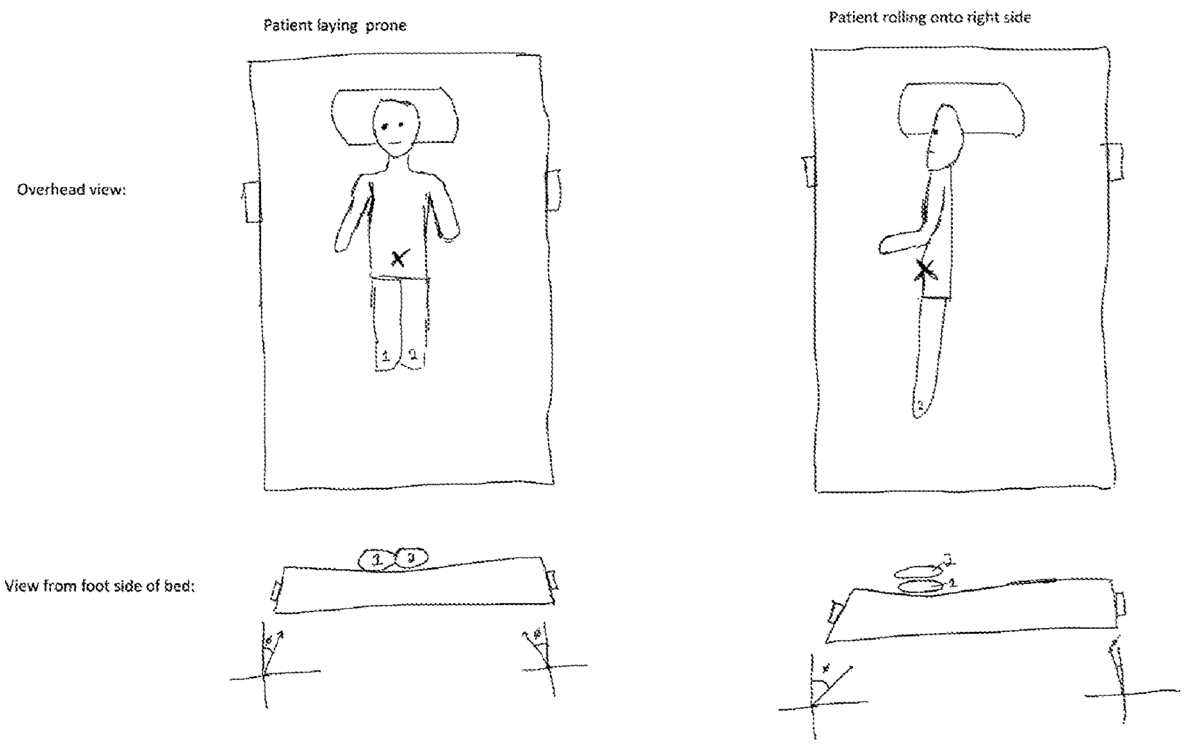
FIG. 8 shows angle of a bed mattress used for gyroscope angle detection.

The accelerometer 102 measures changes in acceleration (m/s2), which is based on how fast or vigorously the patient is moving in bed. The gyroscope 104 measures changes in angle (degrees). Changes in angle of the gyroscope can be used to estimate changes in a patients' position in the mattress. When a patient moves in bed, the mattress deflects or deforms, which in turn changes the angle of the sensor attached to the mattress. As illustrated in FIG. 8, when the patient moves from the prone position to their right side, the sensor angle on the right side of the mattress increases and the sensor angle on the left side of the bed decreases. These changes are measured by the gyroscope, which measures angles in 3D space. In the figure, the X indicates the patient center of mass.

The vibration sensor 108 measures changes in vibration. Any type of movement will be picked up by the vibration sensor 108, which measures general movement of the patient in bed (i.e., the mattress). The microcontroller 110 aggregates data from the three individual sensors 102, 104, 108, and packages it to be transmitted over the communication device 112, which transmits the data to a nearby central data processing unit 150. The central processing unit 150 analyzes the data and transmits information and alerts to the user devices 175, which can be, for example, a hospital networked device or the smart phone of a medical practitioner (e.g., doctor, nurse, staff).

For example, the individual sensors 102, 104, 108, can each be associated with a unique sensor ID. Each sensor 102, 104, 108, detects a condition and transmits the detected condition as a detected signal in real time to the controller 110. Thus, the accelerometer 102 detects acceleration and transmits a detected acceleration value as a detected acceleration signal; the gyroscope 104 detects a rotation/angle and transmits a detected rotation or angle value as a detected rotation/angle signal; and the vibration sensor 108 detects a vibration and transmits a detected vibration value as a detected vibration signal. The detected signals can also include the unique sensor ID and detection time. Each sensor 202 can continuously transmit the detected signal in real time, or can only transmit the detected signal when a change in the detected value is detected, i.e., so that detected signal(s) are only transmitted when the patient moves.

Figure 2B:
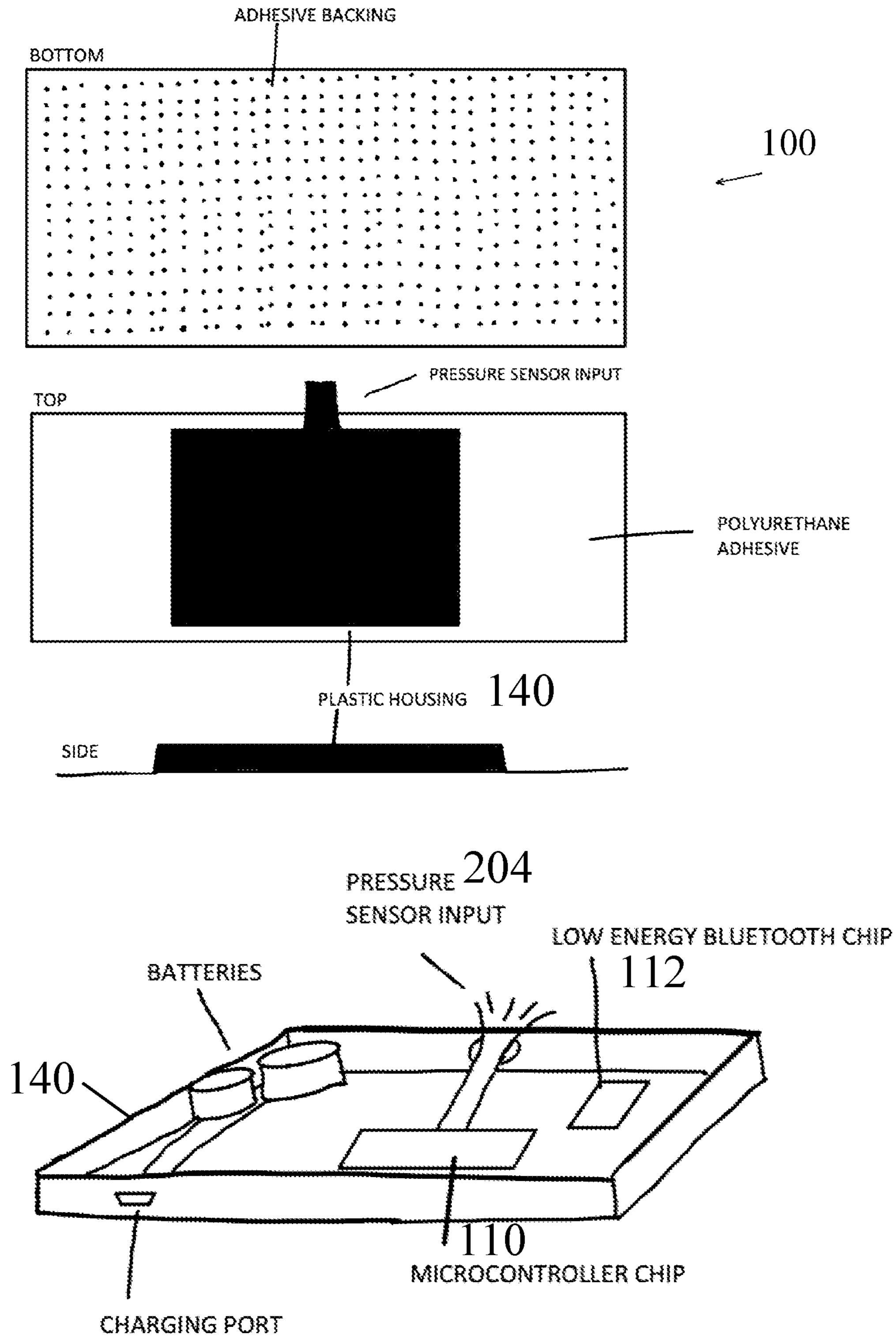
FIG. 2*b* is a block diagram of a wireless sensing apparatus in communication with a pressure sensor array of FIG. 1.

As further shown in the example embodiment of FIGS. 2*a*, 2*b*, the wireless sensor device 100 has several components. It has an adhesive strip (like polyurethane) connected to a plastic housing 140, which contains the electronics. The adhesive strip is attached to the back of the housing 140. The electronics housed in the sensor include but are not limited to an accelerometer 102, gyroscope 104, batteries, low energy Bluetooth module, vibration sensor 108, power supply (batteries), and a microcontroller chip. Information recorded on the sensors are streamed via Bluetooth transceiver 112 to a nearby device which compiles the data and uses an algorithm to determine the motion of the patient in bed.

If the system 6 determines that the patient is immobile for an extended period of time or hasn't changed position in the bed 1, the system 6 generates an alert that notifies hospital or nursing home staff of the patient's immobility. For example, the local microcontroller 110 can determine that the patient is immobile and transmit the alert through the local wireless communication device 112 (here illustrated for example as a Bluetooth transmitter) to an external device, such as for example a phone or bedside monitor. In another embodiment, the central processing unit 150 can determine that the patient is immobile and transmit the alert through the central wireless communication device 156 to the user device 175; i.e., the hospital networked processor such as a medical practitioner device, which can be a nurse's phone or a computer at a nursing station, or directly to the patient's room alert devices.

Patient's mobility scores are generated based on one or more of accelerometer, gyroscope, and vibration data, and are displayed on the user device 175. In other embodiments, the mobility score is directly uploaded to the patient's chart.

Pressure Sensor Grid Unit 200

Referring to FIGS. 1, 2*b*, in certain embodiments, the system 6 can include a pressure sensor grid 200. The pressure sensor grid 200 can be attached to or in contact with, the monitored device 1. In one embodiment, the pressure sensor grid 200 is an array of one or more pressure sensors 202, and a pressure sensor input 204. The input 204 can be a wire that electronically connects the sensor array 202 to the controller 110 of the sensing apparatus 100; though in certain embodiments the input can be a wireless connection. The sensors 202 are arranged in rows and columns to form a square or rectangular shape, though any suitable size and shape can be utilized. The sensors 202 are electronically connected to each other by one or more wires, which can carry power to the sensor 202 and also transmit a detected pressure signal from the sensor 202 to the controller 110 via the input 204. However, in other embodiments, each pressure sensor 202 need not be connected by wire and/or transmit through the input, but can instead, for example, be separate devices with its each of which has its own power supply directly and wired or wirelessly transmit a detected pressure signal to the controller 110.

Each sensor 202 is relatively thin or flat, so that the sensor array 200 does not cause discomfort or otherwise negatively affect the operation of the monitored device 1. As shown, each sensor 202 can have a square or rectangular shape, as shown, though any suitable size and shape can be utilized. As further illustrated, the sensor array 200 has a shape and size that matches and aligns with the shape and size, and fully encompasses at least a portion of the monitored device 1 where the patient engages. In the embodiment of FIG. 1, the sensor array 200 substantially extends the entire width and length of the mattress 1 to detect all movement of the patient in the mattress 1.

As shown, the sensor array 200 can be placed at the bottom surface 5 of the mattress. The sensor array 200 can be a separate device and the mattress 1 placed over the top of the sensor array 200. Or, the sensor array 200 can attach to the mattress 1, such as one or more of the sensors 202 can be affixed directly to the mattress by a fastener or adhesive or the like. Still further, the sensors 202 can be integrally formed with the mattress, either at the bottom surface 5 or internally. Each individual pressure sensor is placed equidistant from the other. In one embodiment, there are 40 pressure sensors that make up the grid to cover a standard size hospital mattress. In other embodiments, there may be more or fewer pressure sensors that make up the grid. The pressure sensors need not extend into the mattress and may be affixed to any part of the bed in any suitable manner, such as by adhesive or fastener.

As shown in FIG. 1, the pressure sensor grid includes multiple pressure sensors 202 placed in a grid on the underside of the mattress. In certain embodiments, the sensors 202 are all connected to the wireless sensing unit 100, which can be attached to the side of the mattress. In other embodiments, the sensors may connect directly with wireless sensing device 100 or be wired directly to the controller 110.

The pressure sensor array 200 transmits signals to the wireless sensing apparatus 100 via the pressure sensor input 204, which are received by the controller 110. Thus, the controller 110 receives incoming data from the individual pressure sensors 202*a*, 202*b*, 202*c* . . . 202*n*, and packages the data into a form that can be sent via low energy Bluetooth module 112 to a nearby central processing unit 150. Pressure sensor 200*n* represents all of the other individual pressure sensors that make up the grid. The individual pressure sensors 202 can be associated with a unique sensor ID. Each sensor 202 detects a pressure and transmits the detected pressure as a detected pressure signal in real time to the controller 110. The detected pressure signal can also include the sensor ID and detection time. Each sensor 202 can continuously transmit the detected pressure signal in real time, or can only transmit the detected pressure signal when a change in the pressure is detected, i.e., so that a detected pressure signal is only transmitted when the patient moves.

The central unit 150 analyzes the detected pressure signals from one or more of the sensors 202 to determine a position and/or movement of the patient. When a patient readjusts their position or is rotated in bed, the force they apply to the underside of the mattress changes. These changes will be measured by the grid of pressure sensors and can be used to assess repositioning. For example, if the patient shifts their weight from the left side of the buttock to the right side, the pressure sensors under the right buttock will read higher pressure measurements than before the movement, and the pressure sensors under the left side will detect a lower pressure than before the movement.

Figure 3B:
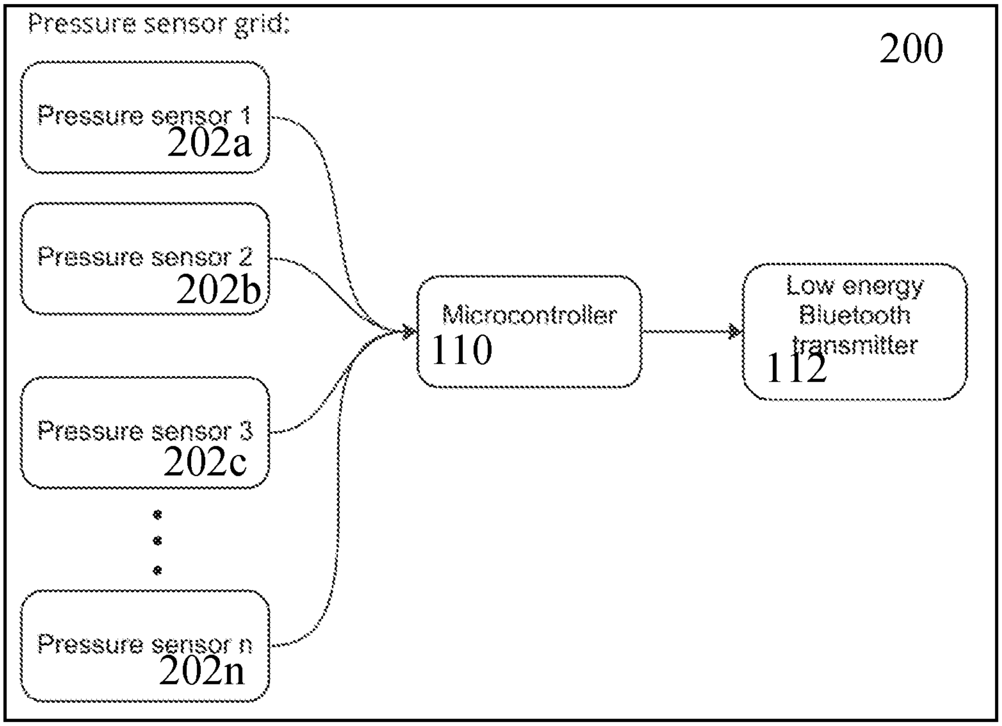
FIG. 3*b* is a block diagram of the wireless sensing apparatus of FIG. 2*b;*

As shown in FIGS. 2*b*, 3*b*, the wireless sensing apparatus 100 is configured for use with the pressure sensing array 200. FIG. 2*b* only utilizes the pressure sensing array 200 to detect movement of the patient, and does not include all of the electronic components of FIG. 2*a*, such as the accelerometer 102, gyroscope 104, and vibration sensor 108. However, in certain embodiments the wireless sensing apparatus 100 can also include one or more accelerometer(s) 102, gyroscope(s) 104, and/or vibration sensor(s) 108 that provide respective sensed signal(s) to the controller 110.

Central Processing Unit 150

Figure 4:
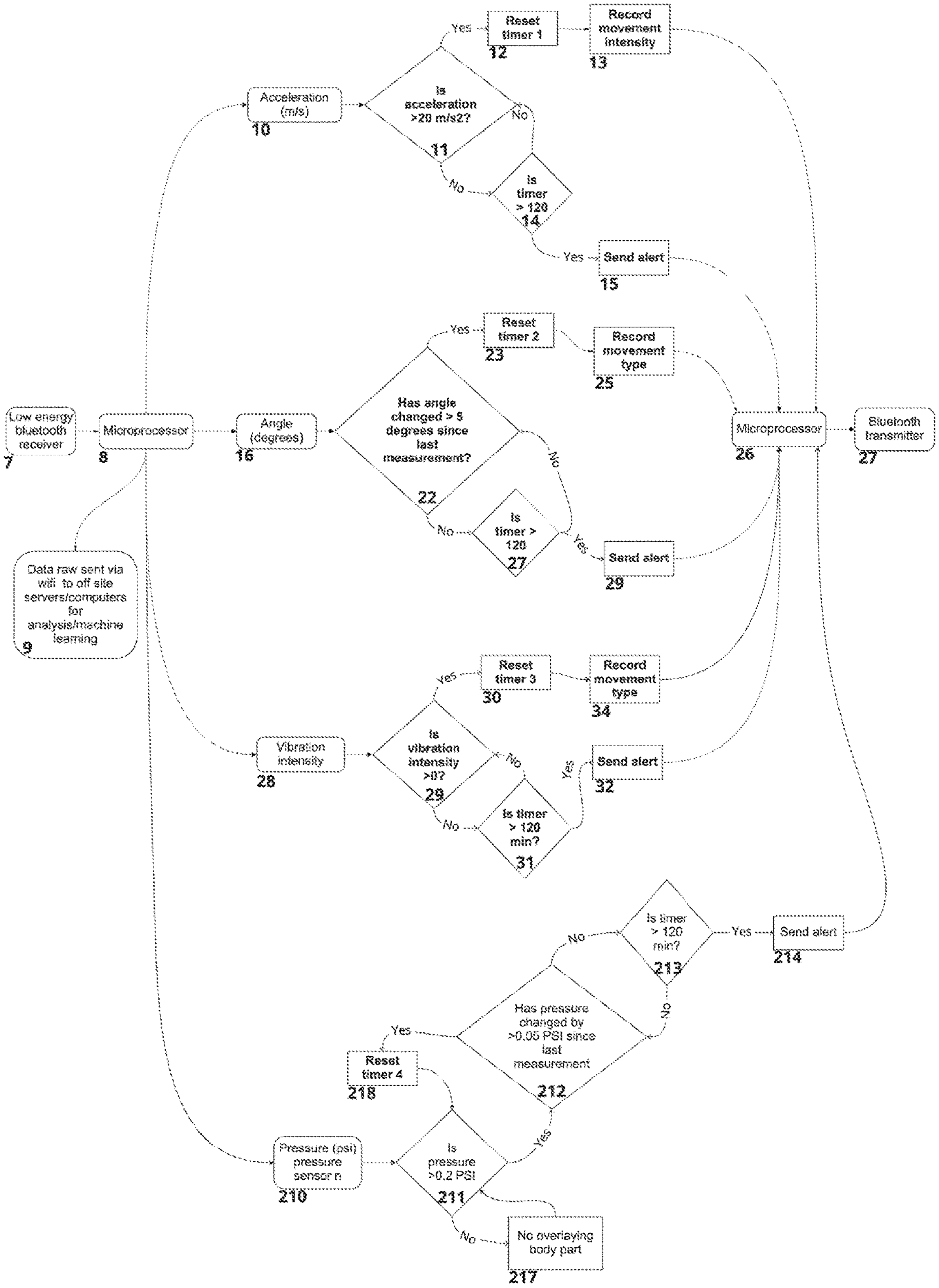
FIG. 4 is a flow diagram showing operation of the pressure sensing system.

Referring now to FIG. 4, an illustrative, non-limiting example of the operation of the central processing unit 150 of the system 6 is shown. The local processing unit 150 can include a local processing device 152, central storage device (e.g., memory), and a local wireless communication device (e.g., a Bluetooth transceiver or receiver and transmitter) that is in wireless communication with the sensor communication device 112. It is noted that though the transmitter and receiver are shown at separate locations in the flow diagram of FIG. 4, those components can be a single component or separate components.

The microcontroller 110 processes and packages the data in a form that can be sent over Bluetooth. The sensors 102, 104, 108, 202 can provide a time stamp, or the microcontroller 110 can add a time stamp. The microcontroller 110 takes the raw data from the detected condition signals of the respective sensors 102, 104, 108, 202, and converts it to a form that can be sent over Bluetooth. At step 7 (FIG. 4), the central Bluetooth receiver at the central processor 150, receives data from the nearby bed sensor device 100 and pressure grid 200. The wireless apparatus 100 unpacks the data received from the sensors via the local microcontroller 110 and transmits the signals to the central processor 150 via the local transmitter 112.

At step 8, the central processing device 152 breaks up the data by sensor type, namely acceleration data, step 10, angle data, step 16, vibration data, step 28, and pressure data, step 210. The central processor 152 performs a series of operations and determines when to send alerts to the external device. Pressure sensor data 210 is divided and operated on for each individual pressure sensor 202*a* . . . 202*n*. So, sensor 202*n* in FIG. 4 represents any of the pressure sensors that are in the grid. The operations below are done continuously for each sensory type, so that the system 6 operates dynamically and in real time. It also sends the raw data to a server over Wi-Fi for analysis and machine learning.

Figure 6:
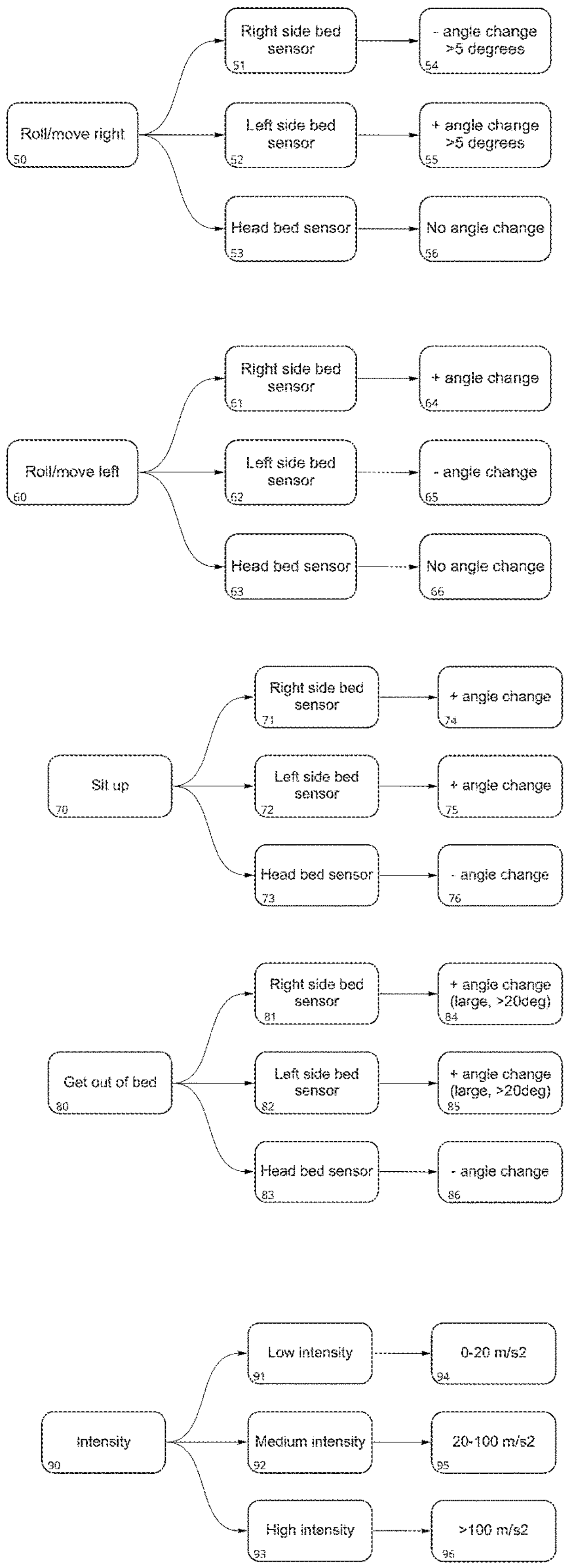
FIG. 6 is a flow diagram of different types of movement detection.

At step 10, the processor 152 receives the detected acceleration signal, and analyzes the data that is received from the accelerator sensor 102. Data fields for sensor 102 include sensor ID, acceleration, and time. The central processor 152 has an internal Timer 1, which it starts, and the central processor 152 determines if the acceleration is greater than 20 m/s (step 11), which indicates that the patient has moved forcefully. Examples of forceful movement include turning over, shifting weight, or getting out of bed. Examples of non-forceful movement include moving arms (but not the torso) to grab an object like a phone or pushing a button, random movements of arms and legs, or moving the head from side to side. If the patient moves forcefully, the Timer 1 is reset (step 12) to 0 and immediately begins counting up. At this time, information about the movement (acceleration, sensor ID, and time is stored at the central processor 152 storage device, step 13, and sent from the central processor 152 to the external medical practitioner device(s) 175 (steps 26, 27), via the transmitter 156. FIG. 6 provides details on how movement intensity is determined.

At steps 11 and 14, the processor 152 waits until a forceful movement is detected. If a forceful movement is not detected in a first predetermined time period (e.g., 120 min) (step14), that indicates that the patient has not moved forcefully (step 11) in that first predetermined time period. Accordingly, the central processor 152 then sends an alert, steps, 15, 26, to the user device(s) 175, via the wireless transmitter 156, step 27. If more than one accelerometer is provided, then the largest measurement of the sensors is used to determine the force of movement. For example, if an accelerometer is provided at the left side of the mattress, the right side of the mattress, and the head of the mattress, and the largest acceleration is measured on the right side of the mattress, then that value is used to determine the force of movement that the patient performed.

At step 16, the central processor 152 processes the detected angle data received from the detected angle signal of the gyroscope sensor 104. Data fields for the gyroscope sensor 104 include sensor ID, sensor angle in reference to horizontal, and time. Here, the central processor 152 has an internal Timer 2, which is started. If the angle of the sensor 104 changes by more than 5 degrees (step 22), then Timer 2 resets (step 23). This indicates the patient has changed position in the bed. When a patient changes their position in bed, this deflects the mattress in a way that changes the angle of the mattress in reference to the horizontal. This change in angle is measured by the gyroscope. Thus, if the patient changes position, the timer is reset to 0 and immediately begins counting up. At this time, information about the movement (sensor ID, sensor angle in reference to the horizontal, and time) is recorded at the central processor unit 150 storage device, step 25, and is also sent to the medical practitioner external device 175 (steps 26, 27). If the Timer 2 has not been reset in a second predetermined period of time (e.g., 120 minutes), step 27, that indicates that the patient has not moved position in the second predetermined time period. The central processor 152 generates an alert, step 29, which is then transmitted to the medical practitioner devices 175, via the transmitter 156, steps 29, 26, 27. FIG. 6 provides more details on how movement type is determined.

If more than one gyroscope sensor 104 is provided, then the largest measurement of the sensors is used to determine the angular movement. For example, if a gyroscope sensor 104 is provided at the left side of the mattress, the right side of the mattress, and the head of the mattress, and the largest angle movement is measured on the right side of the mattress, then that value is used to determine the angle movement that the patient performed.

At step 28, the central processor 152 processes the detected vibration data received from the detected vibration signal of the vibration sensor 108. Data fields for the vibration sensor 108 include sensor ID, vibration sensor voltage, and time. Vibration sensor voltage corresponds to vibration. A higher voltage equates to more vigorous vibration. Zero voltage corresponds to vibration that does not meet the threshold of measurement for sensor 108. The central processor 152 waits to determine if the patient has moved any part of their body. This sensor detects non-specific movement and may be used to assess general movement. If the vibration data detects an intensity greater than zero, that indicates that the patient has moved any part of their body. Accordingly, the central processor 152 has an internal Timer 3, which is started. At step 29, if the vibration sensor 108 measures a non-zero vibration, the Timer 3 is reset (step 30) to zero and immediately begins counting up. The central processor 152 records the movement data (vibration intensity and sensor location that transmitted the signal) at its storage device, step 34, and transmits the movement data to the medical practitioner external device(s) 175 (steps 26, 27). If the Timer 3 has not been reset in a third predetermined time period (e.g., 120 minutes), steps 29, 31, that indicates that the patient has not moved in the third time period. The central processor 150 then generates an alert, step 32, and transmits the alert to the medical practitioner external device(s) 175, via the wireless transmitter, steps 32, 26, 27.

If more than one vibration sensor 108 is provided, then the largest measurement of the sensors is used to determine the force of movement. For example, if a vibration sensor 108 is provided at the left side of the mattress, the right side of the mattress, and the head of the mattress, and the largest vibration is measured on the right side of the mattress, then that value is used to determine the force of movement that the patient performed.

Accordingly, the microprocessor 152 collects the data to be transmitted to the external device(s) 175 (alert, movement types) and packages it to be transmitted via Bluetooth. It tells the external device(s) 175 the time the alert was generated and the last time the patient moved. At step 27, the Bluetooth transmitter 154 sends this data to the external device(s) 175, step 27.

At step 210, the pressure reading for a pressure sensor 202 is read. All pressure sensors 202 are read in parallel and analyzed in the same way. The central processor 152 receives the detected pressure data from the detected pressure signal of the pressure sensor(s) 202. Data fields for pressure sensor 202 include sensor ID, pressure, and time. The central processor 152 has an internal Timer 4, which it starts, and the central processor 152 determines if the pressure is greater than 0.2 PSI (step 211), it continues on in the process. A pressure reading above 0.2 PSI means that a part of the patient's body is overlaying the particular pressure sensor 202. A pressure reading less than 0.2 PSI is caused solely by the weight of the mattress overlaying the pressure sensor (step 217), which can be zeroed out if desired (so that, for example, the pressure sensor 202 reads 0.0 PSI when the mattress is in place). In other embodiments, this baseline pressure is more or less than 0.2 PSI. This step ensures alerts are not generated when a section of the mattress does not have a body part on it and thus has no changes in pressure over an extended period of time.

In step 212, if the pressure has changed by more than 0.05 PSI since the last measurement, the timer is reset (step 218). If the pressure has not changed by more than 0.05 PSI and it has been more than 120 min since timer 4 was last reset (step 213), an alert is generated (step 214). The threshold of 0.05 PSI is set for what is considered to be a significant movement, though in other embodiments this pressure may be higher or lower. Examples of significant movement include, for example, turning over, shifting weight, or getting out of bed. Any pressure change less than 0.05 PSI does not signify significant movement and means that the patient did not shift onto or off the pressure sensor (i.e., the patient has not moved). If the pressure sensor reading has changed by more than 0.05 PSI since the last reading, information about the movement (sensor ID, pressure, time) and the alert is sent to processor unit 150 storage device and is also sent to the medical practitioner external device 175 (steps 26, 27). And, the greatest pressure measured by any of the pressure sensors 202*a* . . . 202*n* of the pressure sensor array 200, is utilized. So that if any one of the pressure sensors 202*a* . . . 202*n* measures a pressure change of more than 0.05 PSI, the Timer 4 is reset.

It is noted that in the example operation shown in FIG. 4, the acceleration data (step 10), angle data (step 16), vibration data (step 28), and/or pressure data (step 210), are separately (but simultaneously) analyzed by the central processor 152, and an alert is generated in real time and without delay or manual interaction. And an alert (steps 15, 29, 32, 214) is generated if any one of the first, second, third, or fourth predetermined time periods are exceeded (steps 14, 27, 31, 213). Thus, the central processor 152 will generate an alarm if the user hasn't moved forcefully (step 15), changed position (step 29), or moved (step 32, 214) in the first, second, third or fourth time periods. It is noted that the first, second, third and fourth time periods are independent of one another, and do not necessarily start and/or stop at the same time but instead can be offset from each other. In addition, the first, second, third and fourth time periods can be the same amount of time or different amounts of time. Thus, for example, if the user moves forcefully (step 11), but does not change positions (step 22) or moved (steps 29, 212), the central processor 152 will generate an alert that the patient has not changed positions, step 29. And, the forceful movement will reset the first time period of Timer 1, step 12, but will not reset the second, third or fourth time periods of Timers 2, 3, 4, steps 22, 29, 211. Still further, the processor 152 can determine a specific corrective action to be taken. For example, if the central processor 152 determines that the user has moved their legs but not their torso, the central processor 152 can adjust the torso portion of the mattress; or indicate to the user device 175 that the torso portion of the mattress be adjusted.

However, in other example embodiments, the central processor 152 can generate an alert only when two, three, or all four conditions are met. That is, an alert can be generated if the user either moves forcefully, step 11, or if the user changes position, step 22. If either of those conditions are met, both the first and second predetermined time periods, Timers 1, 2, can be reset, and no alert is generated. Still further, the microprocessor 110 and/or central processor 152 can receive data from other medical devices, such as a respirator, blood pressure cuff, or CPAP machine, to further determine whether or not an alert should be generated, and what type of corrective action should be taken, if any.

Still further, the alert and/or corrective action can be based, at least in part, on the type of illness or medical condition of the patient and patient data (age, sex, weight, etc.). For example, the threshold levels and/or time periods can be different for a patient having a broken leg, than for a patient having a respiratory condition.

It is further noted that the operation of FIG. 4 is described with respect to the central processing unit 150. The central processing unit 150 can be located in the patient's room, at the end of the hall, or anywhere in the hospital, and communicate with multiple hospital beds. Though Bluetooth is illustrated, other wireless formats can be utilized, such as radio frequency (RF), or information can be communicated through a router in the patient's room to the central processing unit 150 located on the floor or elsewhere in the building. Moreover, while the operation of FIG. 4 is described as being implemented by the central processor 152, it can occur at the microprocessor 110 or at the user device 175.

External User Device 175

Figure 5:
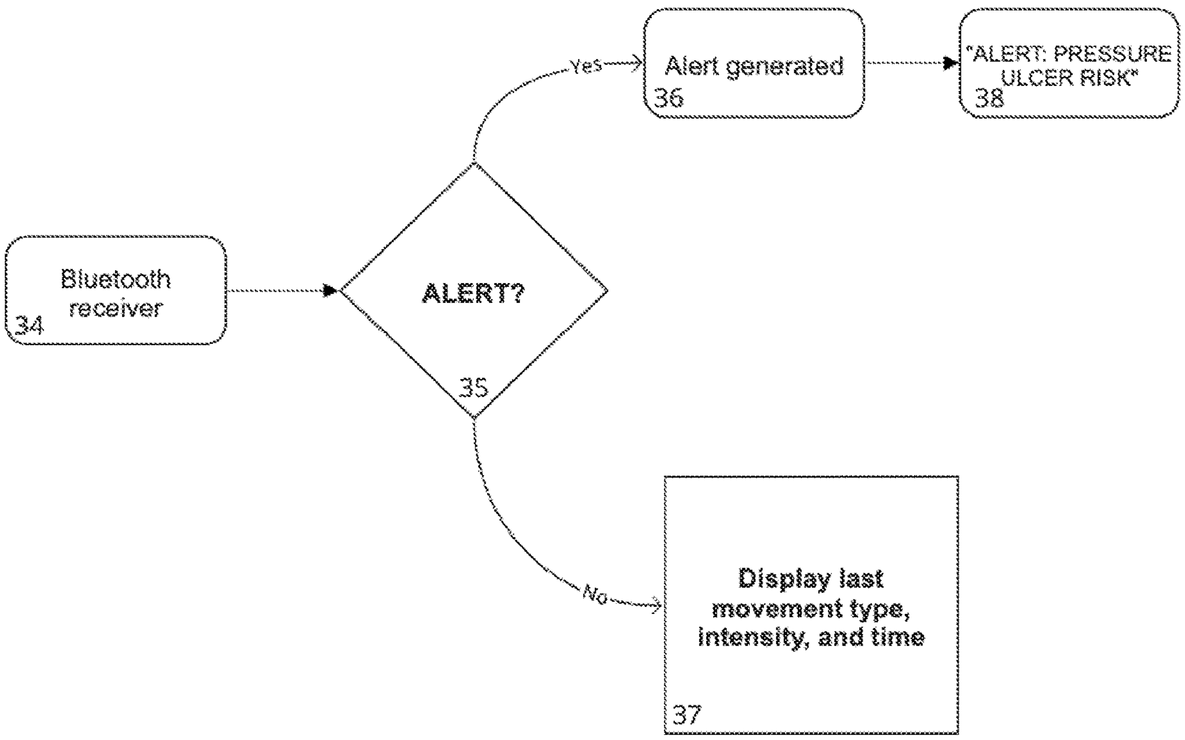
FIG. 5 is a flow diagram of the user device operation.

Turning to FIG. 5, example operation at the user device 175 is illustrated. Here, the user device 175 can be, for example, a hospital networked device or the smart phone of a medical practitioner (e.g., doctor, nurse, staff) or a computer at a nursing station, or directly to the patient's room alert devices. The external user device 175 includes a processor and a wireless communication device, such as a Bluetooth transceiver 34 (iPhone, bedside monitor, patient chart or other device) that receives data from the external data processing unit. The user device receives data, including for example, whether or not an alert has been generated, by which sensor and which sensor type, types of movement patient has undergone, and values for each sensor that have been transmitted, as well as the status of the various sensors and the last time that sensor was activated by patient movement.

Figure 7:
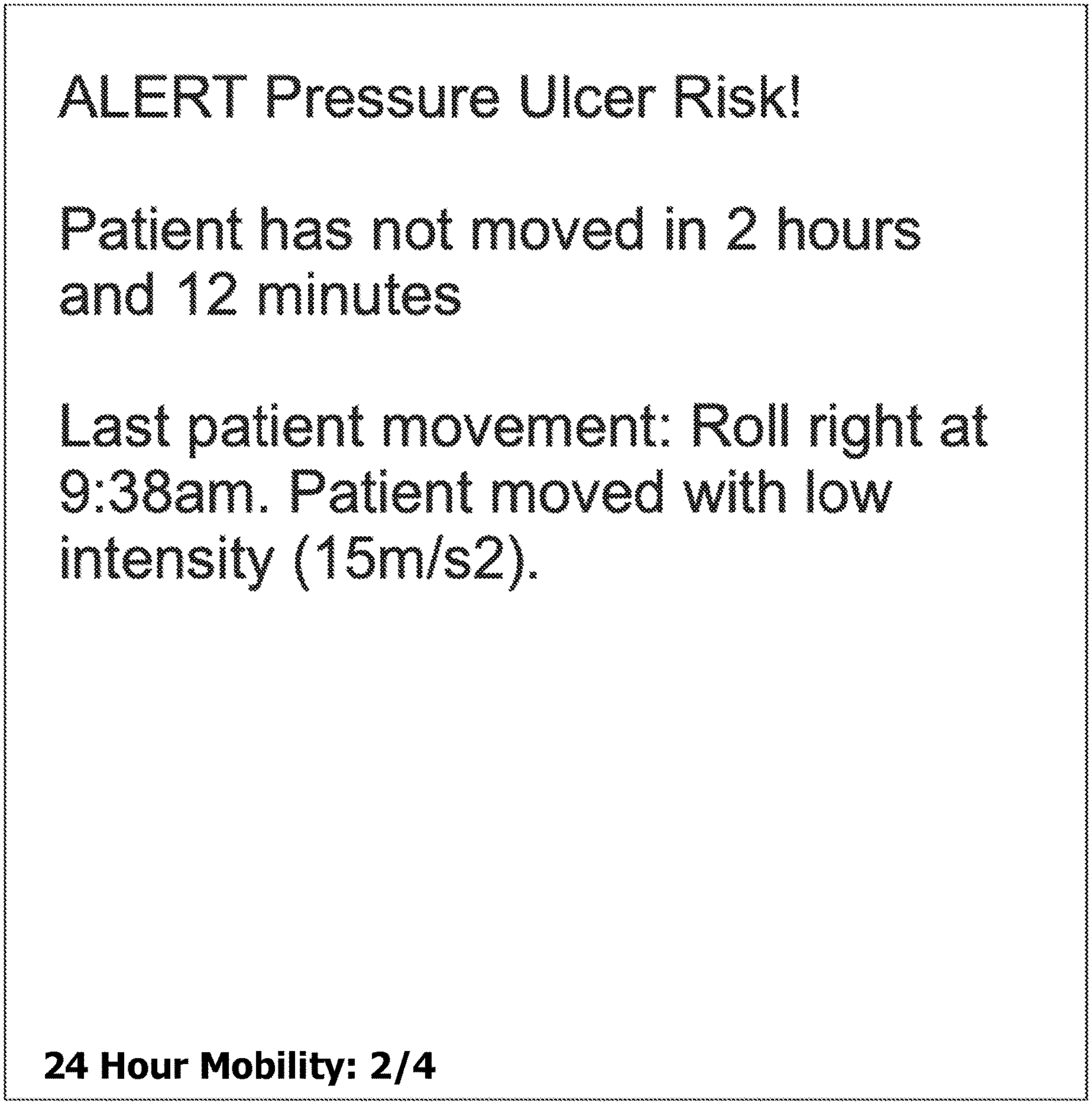
FIG. 7 shows an alert at the user device with mobility score.

At step 35, if an alert has been generated, step 36, the external device displays the alert, step 38. FIG. 7 is an example alert message. It also displays the last time the patient moved and the time the alert was generated. Nursing staff can then move the patient so that they do not get a pressure ulcer. In addition, the user device 175 can be one or more machine(s) or other device(s) that provides a corrective action in response to the alert, either simultaneously or in series. For example, the machine can be the hospital bed that moves the mattress, so that the central processing unit 150 can control the bed to raise or lower the feet or torso portions of the mattress; or the machine can be leg cuffs that apply/release a pressure to the legs or other parts of the patient body; or the machine can be a medication apparatus that increases or decreases medication (such as pain medication). Operation of the machine(s) occur dynamically in response to the detected conditions, and in real time. The machines can be in direct communication with the central processing unit 150 and/or the user device 175, and can be directly controlled by the central processor unit 150, or by the user device 175.

If no alert has been generated, step 37, the external device displays the patients last movement type, time, and other sensor parameters that are received. Nursing staff can use this information to assess the mobility of the patient.

The user device 175 can also be utilized to control operation of the sensors 102, 104, 108, 202, central processing unit 150, and/or wireless sensing apparatus 100. For example, the user device processor can be used to adjust the various timing periods of Timers 1, 2, 3, 4 (steps 14, 27, 31, 213), or the threshold levels (steps 11, 22, 29, 212), and/or the weight given to each sensor (steps 10, 16, 28, 210) in determining whether an alert or corrective action should be taken, or what type of action should be taken.

Movement Types

FIG. 6 shows characteristics of different movements. At step 50, the central processing 152 determines that the patient has rolled or moved to the right. Here, the patient changes position by rolling or moving to their right. This is recorded by the gyroscope sensor 104. During this type of movement, gyroscope sensor 104 of the sensing device 100 attached to the right side of the hospital bed 1, step 51, has a negative change in angle of more than 5 degrees, step 54; the gyroscopic sensor 104 of the sensing device 100 attached to the left side of the hospital bed 1, step 52, has a positive change in angle of more than 5 degrees, step 55; and the gyroscopic sensor 104 for the sensing device 100 attached to the head of the hospital bed 1, step 53, has a negligible angle change (a change in angle less than 5 degrees), step 56.

At step 60, the central processing 152 determines that the patient has rolled or moved to the left. This is recorded by the gyroscope component 104 of the sensing device 100. During this type of movement, the sensor 104 attached to the right side of the hospital bed 1, step 61, has a negative change in angle of more than 5 degrees, step 64; the sensor 104 attached to the left side of the hospital bed 1, step 62, has a positive change in angle of more than 5 degrees, step 65; and the sensor 104 attached to the head of the hospital bed 1, step 63, has a negligible angle change (a change in angle less than 5 degrees), step 66.

At step 70, the central processing 152 determines that the patient has changed position by sitting up. This is recorded by the gyroscope component 104 of the sensing device 100. During this type of movement, the sensor 104 attached to the right side of the hospital bed 1, step 71, has a positive change in angle of more than 5 degrees, step 74; the sensor 104 attached to the left side of the hospital bed 1, step 72, has a positive change in angle of more than 5 degrees, step 75; and the sensor 104 attached to the head of the hospital bed 1, step 73, has an angle change of more than 5 degrees, step 76.

At step 80, the central processing 152 determines that the patient has changed position by sitting up and getting out of bed 1. This is recorded by the gyroscope component 104 of the sensing device 100. During this type of movement, the sensor 104 attached to the right side of the hospital bed, step 81, has a positive change in angle of more than 20 degrees, step 84; the sensor 104 attached to the left side of the hospital bed 1, step 82, has a positive change in angle of more than 20 degrees, step 85; and the sensor 104 attached to the head of the hospital bed 1, step 83, has an angle change of more than 5 degrees, step 86.

At step 90, the central processing 152 determines the intensity of movement. A characteristic of movement that describes how vigorously the patient moves. This characteristic of movement is recorded by the accelerometer sensor 102 of the sensing device 100. Low intensity movement, step 91, is movement that causes an accelerometer 102 reading lower than 20 m/s2, step 94. A low intensity movement may be a patient shifting the position their arm in bed in order to grab a remote. Medium intensity movement, step 92, is movement that causes an accelerometer reading between 20-100 m/s2 (95). A medium intensity movement may be an elderly patient slowly sitting up in bed. And high intensity movement, step 93, is movement that causes an accelerometer reading between greater than 100 m/s2, step 96. A high intensity movement may be a young healthy patient rolling from prone onto their right side. While it is noted that the operation above (FIG. 3, step 11) has a threshold level set for forceful movement at a medium intensity, any suitable level can be set depending on the condition of the patient. And, the central processor 152 can store any movement intensity for review by the user device 175. And, different levels can be combined with other movement activities. For example, a low intensity movement combined with a change in position, can be utilized to avoid an alert of intensity and/or change in position.

FIG. 7 shows an example alert at the user device 175, and data about the patient's movement. The 24 hour mobility: 2/4 is the mobility score. This aligns with what nursing staff use to assess mobility on the Braden score tool. It is a scale from 1 to 4. 1 being completely immobile, 4 being no limitations. The score gives the providers a numeric score that shows overall how active a patient is at that time or day.

Algorithm

The external device 150 that receives data from the sensors 102, 104, 108 (via the local controller 110, local transmitter 112, and the central receiver 154) use an algorithm to interpret the motion of the patient in bed. It uses angular acceleration, sensor angle, vibration, and other data collected by the sensors to interpret motion. For example, sensor angle changes when a patient changes position in bed and angular acceleration changes can be used to assess how vigorously the patient is moving. When the patient has not changed position in a significant amount of time (e.g., 2 hours), the external device will send an alert to a bed side monitor or phone app so it can be seen by hospital staff. Another potential feature is that the change in position information can be directly uploaded to the patient's chart, so it can be easily accessed by any healthcare provider with access to the patient's chart.

Another feature of the device may be a machine learning capability, where incoming data is correlated with specific diseases or conditions with which the patient is experiencing. For this, patient information and data from their charts would be collected, and their patterns of movement would be analyzed. Using this data, machine learning algorithms would learn what types and patterns of movement correlate with certain disease states. Then, the machine learning algorithm would be used to predict these same events in other patients. For example, consider a patient that experienced a seizure. If the seizure was recorded in the patient's chart, the machine learning algorithm would retrospectively analyze their movement during the time that the seizure took place. After collecting and analyzing data from many patients' certain patterns of movement that are indicative of a seizure would be learned by the machine learning algorithm. Then, recognition of this pattern by the machine learning algorithm would later be applied to alert staff to a patient having a seizure.

In addition, the central processor 152 can also condition a given alert on the number of movements in a given predetermined period of time. For example, it can require 2 forceful movements be detected by the accelerometer 102 in the first time period, or 3 low intensity movements, or 1 high intensity movement.

It is further noted that a vibration sensor 108 and accelerometer 102 need not be provided in each sensing device 100. Rather, it is sufficient if a single sensing device 100 have a vibration sensor 108 (or a pressure sensor array 200) and a single sending device 100 have an accelerometer 102, for a given bed mattress. That is, only a single vibration sensor 108 is needed to detect movement and only a single accelerometer 102 is needed to detect movement intensity. Thus, the vibration sensor 108 and accelerometer 102 can be located at any position on the bed mattress, such as at the left side, right side, head end side, or foot end side, and need not be provided at multiple sides of the bed mattress. One added benefit of the accelerometer is measuring how vigorous the movement is, which may be important for the medical practitioner. And the vibration sensor and/or pressure sensors may offer another layer of security in case the other sensors fail.

Information about the patient, including but not limited to age, weight, height, and sex are used to customize the algorithm for individual patients. For example, lighter patients may require the algorithm to be more sensitive to changes in the accelerometer, gyroscope, and vibration to accurately detect movement. The provider may input this patient specific information, or it may be automatically uploaded from their chart.

Finally, the device calculates mobility scores that are calculated using information from the sensors that can be used to predict patient risk for developing pressure injuries.

Uses

One example application of the system is to collect data and look for patterns that represent a disease state, such as pressure injuries. Once it recognizes a pattern (limited movement) it can alert nursing staff so that earlier interventions (rotating patient) can be implemented to prevent the disease. The data can be used for early intervention. As another example, certain patterns of movement could be recognized as a seizure and physicians/nurses could be notified so that early interventions could be used to mitigate future seizures and/or complications.

One main intended use of the device is to prevent pressure injuries (bed sores) from forming. Bed sores form when patients are immobile and lay on the same area of skin for an extended period of time—usually more than several hours. So, alerts will allow nursing staff to turn patients before bed sores form. In addition, the device may allow for more accurate assessment of patient's mobility. In most settings, staff provides subjective mobility assessments in order to gauge a patient's risk for developing pressure injuries. Variability between staff members, staff inexperience, and acute changes in mobility status (e.g., delirium) can all affect the accuracy of these subjective mobility assessments. This can lead to at risk patients not being correctly identified. The device can also be used for other conditions that are caused by immobility or where immobility is a risk factor, like deep veinous thrombosis and delirium.

The system can apply to hospitals, and also to sites outside of hospitals, like in-home healthcare. In this setting the sensors would be attached to beds and wheelchairs in a patient's home to alert them (or their primary care givers) of their immobility.

It is further noted that the array 200 is of pressure sensors. However, the array can include other sensors, such as vibration sensors or a combination of pressure and vibration sensors.

The system and method of the present disclosure include operation by one or more processing devices, including the local controller 110, and a central processing device 150, and at the user device 175. It is noted that the processing devices can be any suitable device, such as a computer, server, mainframe, processor, microprocessor, controller, PC, tablet, smartphone, or the like. The processing devices can be used in combination with other suitable components, such as a display device (monitor, LED screen, digital screen, etc.), memory or storage device, input device (touchscreen, keyboard, pointing device such as a mouse), wireless module (for RF, Bluetooth, infrared, WiFi, etc.). The information may be stored on a computer medium such as a computer hard drive, on a CD ROM disk or on any other appropriate data storage device, which can be located at or in communication with the processing device. The entire process is conducted automatically by the processing device, and without any manual interaction. Accordingly, unless indicated otherwise the process can occur substantially in real-time without any delays or manual action. In addition, the system operates dynamically; for example, the various modules continually receive data and information and continually determine the patient's movement.

The statements made with respect to one embodiment apply to the other embodiments, unless otherwise specifically noted. It is further understood that the description and scope of invention apply equally (though the descriptions have not been repeated) for each structure that is the same or similar between each of the various embodiment, and whether or not those structures have been assigned a similar reference numeral.

The foregoing description and drawings should be considered as illustrative only of the principles of the disclosure, which may be configured in a variety of shapes and sizes and is not intended to be limited by the embodiment herein described. Numerous applications of the disclosure will readily occur to those skilled in the art. Therefore, it is not desired to limit the disclosure to the specific examples disclosed or the exact construction and operation shown and described. Rather, all suitable modifications and equivalents may be resorted to, falling within the scope of the disclosure.

The invention claimed is:

1. A patient movement monitoring system for a bed mattress having a first side, a second side, a head end side and a foot end, said system comprising:

a first sensing device coupled at the first side of the bed mattress;

a second sensing device coupled at the second side of the bed mattress;

a third sensing device coupled at the head end side of the bed mattress;

wherein said first sensing device, said second sensing device, and said third sensing device each include at least one of:

an accelerometer configured to detect an intensity of patient movement in the bed mattress and provide an accelerometer output signal indicating said intensity;

a gyroscope configured to detect an angle of the bed mattress and provide a gyroscope output signal indicating said angle;

a vibration sensor configured to detect vibration of the bed mattress and provide a vibration output signal indicating said vibration;

a fourth sensing device coupled at the underside of the bed mattress, said fourth sensing device comprising a pressure sensor array having one or more pressure sensors each configured to detect changes in pressure of the bed mattress and provide a pressure output signal indicating said pressure change; and a processing device in electronic communication with said first sensing device, said second sensing device, said third sensing device, and said fourth sensing device, said processing device configured to receive the acceleration output signal from said accelerometer and generate a first alert if said accelerometer does not detect a minimum intensity of patient movement within a first predetermined time period; said processing device configured to receive the gyroscope output signal from said gyroscope and generate a second alert if said gyroscope does not detect a threshold patient movement within a second predetermined time period; said processing device configured to receive a vibration output signal from said vibration sensor and generate a third alert if said vibration sensor does not detect a threshold vibration within a third predetermined time period; and said processing device configured to receive a pressure output signal from said pressure sensor array and generate a fourth alert if said one or more pressure sensors do not detect a change in pressure within a fourth predetermined time period.

2. The patient movement monitoring system of claim 1, wherein said first side comprises a left side, and said second side comprises a right side.

3. The patient movement monitoring system of claim 1, the bed mattress having a top surface and a bottom surface, wherein said first side, second side, and head end side are between the top surface and the bottom surface.

4. The patient movement monitoring system of claim 1, further comprising a first sensor housing enclosing said first sensing device, a second sensor housing enclosing said second sensing device, a third sensor housing enclosing said third sensing device, and a fourth sensor housing enclosing said fourth sensing device.

5. The patient movement monitoring system of claim 1, wherein said processing device is remotely located and each of said first sensing device, second sensing device, third sensing device, and fourth sensing device further comprising a controller configured to receive the accelerometer output signal, gyroscope output signal, vibration output signal, and pressure signal, and a wireless transmitter in communication with said controller and configured to wirelessly transmit the accelerometer output signal, gyroscope output signal, vibration output signal, and pressure output signal to said processing device.

6. The patient movement monitoring system of claim 1, wherein said gyroscope measures deflection of the bed mattress to assess movement and predict patient outcomes.

7. The patient movement monitoring system of claim 1, wherein said processing device uses machine learning to predict patient outcomes in any form.

8. The patient movement monitoring system of claim 1, wherein said first sensing device, said second sensing device, and said third sensing device each include the accelerometer, the gyroscope and the vibration sensor.

9. The patient movement monitoring system of claim 1, wherein said processing device generates a corrective action based on the detected intensity, detected angle, detected vibration and/or detected pressure.

10. The patient movement monitoring system of claim 9, wherein the corrective action is further based on a patient condition.

11. The patient movement monitoring system of claim 10, wherein the patient condition comprises one of age, health, and illness.

12. The patient movement monitoring system of claim 9, further comprising a medical device in electronic communication with said processing device, said processing device configured to control said medical device to apply the corrective action.

13. The patient movement monitoring system of claim 12, wherein said medical device comprises a bed, and said processing device adjusts a position of said bed.

14. The patient movement monitoring system of claim 9, wherein said processing device is further configured to control a medical device to apply the corrective action.

15. The patient movement monitoring system of claim 12, wherein the medical device comprises any one of a blood pressure cuff, hospital bed, and/or respirator.

16. A patient movement monitoring system for a bed mattress having a first side, a second side, a head end side and a foot end, said system comprising:

one or more sensing devices coupled at one or more of the first side, the second side, and/or the head end side of the bed mattress, wherein said one or more sensing devices each includes at least one of:

an accelerometer configured to detect an intensity of patient movement in the bed mattress and provide an accelerometer output signal indicating said intensity;

a gyroscope configured to detect an angle of the bed mattress and provide a gyroscope output signal indicating said angle; or a vibration sensor configured to detect vibration of the bed mattress and provide a vibration output signal indicating said vibration;

a pressure sensor array coupled at the underside of the bed mattress, said pressure sensor array having one or more pressure sensors each configured to detect changes in pressure of the bed mattress and provide a pressure output signal indicating said pressure change; and a processing device in electronic communication with said one or more sensing devices, and said pressure sensor array, said processing device configured to:

if said one or more sensing devices has the accelerometer, receive the acceleration output signal from said accelerometer and generate a first alert if said accelerometer does not detect a minimum intensity of patient movement within a first predetermined time period;

if said one or more sensing devices has the gyroscope, receive the gyroscope output signal from said gyroscope and generate a second alert if said gyroscope does not detect a threshold patient movement within a second predetermined time period;

if said one or more sensing devices has the vibration sensor, receive a vibration output signal from said vibration sensor and generate a third alert if said vibration sensor does not detect a threshold vibration within a third predetermined time period; and said processing device configured to receive a pressure output signal from said pressure sensor array and generate a fourth alert if said one or more pressure sensors does not detect a change in pressure within a fourth predetermined time period.

17. The patient movement monitoring system of claim 16, wherein at least one of said one or more sensing devices includes the accelerometer, at least one of said one or more sensing devices includes the gyroscope, and at least one of said one or more sensing devices includes the vibration sensor.

* * * * *